US011361441B2

(12) United States Patent
Kim et al.

(10) Patent No.: US 11,361,441 B2
(45) Date of Patent: Jun. 14, 2022

(54) METHOD FOR DETERMINING WHETHER EXAMINEE IS INFECTED BY MICROORGANISM AND APPARATUS USING THE SAME

(71) Applicant: Vuno, Inc., Seoul (KR)

(72) Inventors: Hyun-Jun Kim, Yongin Gyeonggi-do (KR); Yeha Lee, Hwaseong Gyeonggi-do (KR)

(73) Assignee: Vuno, Inc., Seoul (KR)

( * ) Notice: Subject to any disclaimer, the term of this patent is extended or adjusted under 35 U.S.C. 154(b) by 190 days.

(21) Appl. No.: 16/618,488

(22) PCT Filed: Jan. 4, 2018

(86) PCT No.: PCT/KR2018/000212
§ 371 (c)(1),
(2) Date: Dec. 2, 2019

(87) PCT Pub. No.: WO2018/221816
PCT Pub. Date: Dec. 6, 2018

(65) Prior Publication Data
US 2020/0273173 A1 Aug. 27, 2020

(30) Foreign Application Priority Data
May 31, 2017 (KR) .................. 10-2017-0067838

(51) Int. Cl.
*G06K 9/00* (2006.01)
*G06T 7/00* (2017.01)
(Continued)

(52) U.S. Cl.
CPC .......... *G06T 7/0014* (2013.01); *G06N 3/08* (2013.01); *G16H 30/40* (2018.01); *G16H 50/20* (2018.01);
(Continued)

(58) Field of Classification Search
CPC ................ G06N 3/0454; G06N 3/08; G06T 2207/10056; G06T 2207/30004;
(Continued)

(56) References Cited

U.S. PATENT DOCUMENTS 10,803,616 B1 * 10/2020 Twigg ................ G06K 9/00389
2012/0169863 A1 * 7/2012 Bachelet ........... B01L 3/502715
348/79
(Continued)

FOREIGN PATENT DOCUMENTS

KR  1020090010555 A  1/2009
KR  1020140091176 A  7/2014
(Continued)

OTHER PUBLICATIONS

Asherons, "Trichomonas Vaginitis Causes symptoms and Treatment", Mar. 10, 2017, p. 1-4, Blog from internet <http://jeongil13579.com/195>.
International Search Report dated Apr. 4, 2018.

*Primary Examiner* — Xin Jia
(74) *Attorney, Agent, or Firm* — IP & T Group LLP

(57) ABSTRACT

Provided are a method for determining whether an examinee is infected by microorganism, and a determination apparatus using the same. Specifically, the determination apparatus according to the present invention obtains an microphotographed image of a biological sample of the examinee; receives the obtained microphotographed image and generates analysis information on the microorganism based on a deep learning model of the examinee; visualize the generated analysis information to provide it, so as to perform at least one of (i) a process of supporting a remote reading on whether the microorganism corresponding to the analysis information exists or not, and (ii) a process of supporting a user of the computing apparatus to read whether the micro- (Continued)

organism corresponding to the analysis information exists or not; and provides a final result as its result.

14 Claims, 4 Drawing Sheets

(51) Int. Cl.
| | | |
|---|---|---|
| *G16H 50/50* | (2018.01) | |
| *G16H 50/20* | (2018.01) | |
| *G16H 30/40* | (2018.01) | |
| *G06N 3/08* | (2006.01) | |
| *G06N 3/04* | (2006.01) | |

(52) U.S. Cl.
CPC ........... *G16H 50/50* (2018.01); *G06N 3/0454* (2013.01); *G06T 2207/10056* (2013.01); *G06T 2207/30004* (2013.01)

(58) Field of Classification Search
CPC ...... G06T 7/0014; G16B 40/00; G16B 45/00; G16H 30/40; G16H 50/20; G16H 50/50
See application file for complete search history.

(56) References Cited

U.S. PATENT DOCUMENTS

| | | | |
|---|---|---|---|
| 2013/0071875 A1* | 3/2013 | Zemer | ........................ G06T 7/70 |
| | | | 435/34 |
| 2018/0211380 A1* | 7/2018 | Tandon | ................. G06K 9/6271 |
| 2020/0300750 A1* | 9/2020 | Eshel | ..................... G01N 33/49 |

FOREIGN PATENT DOCUMENTS

| | | |
|---|---|---|
| KR | 101725125 B1 | 4/2017 |
| KR | 1020170047423 A | 5/2017 |

* cited by examiner

[Fig. 1]
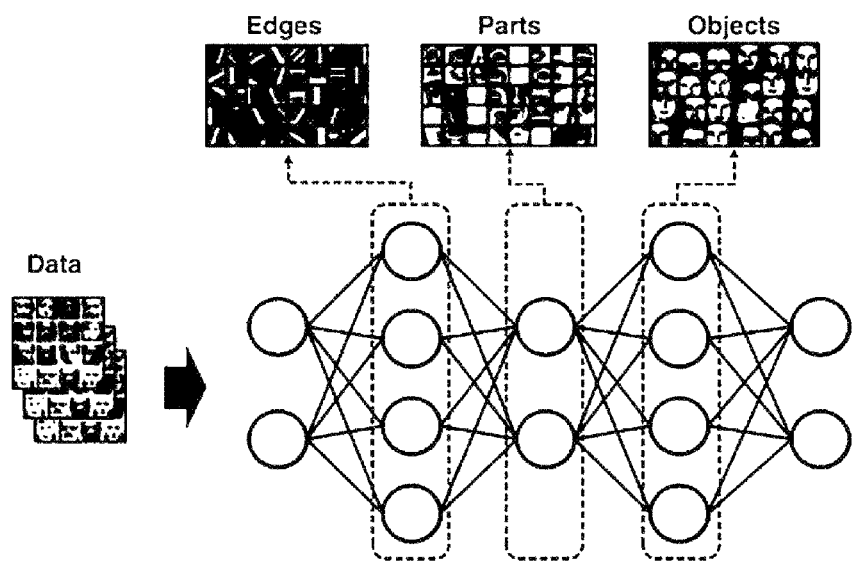
[Fig. 2]
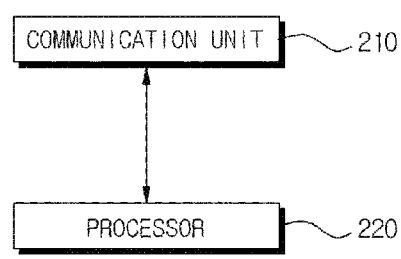

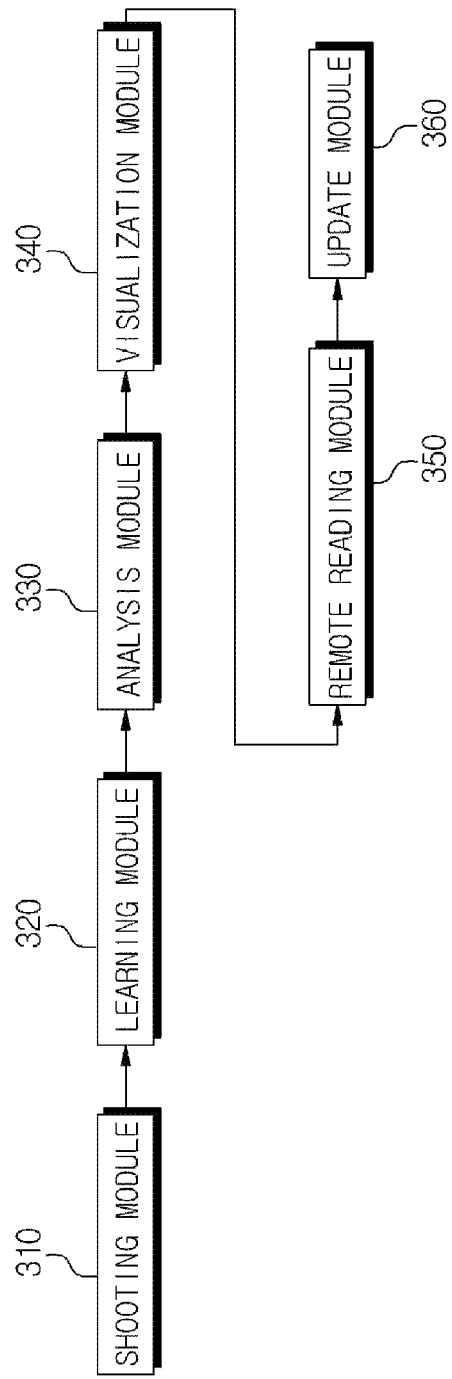

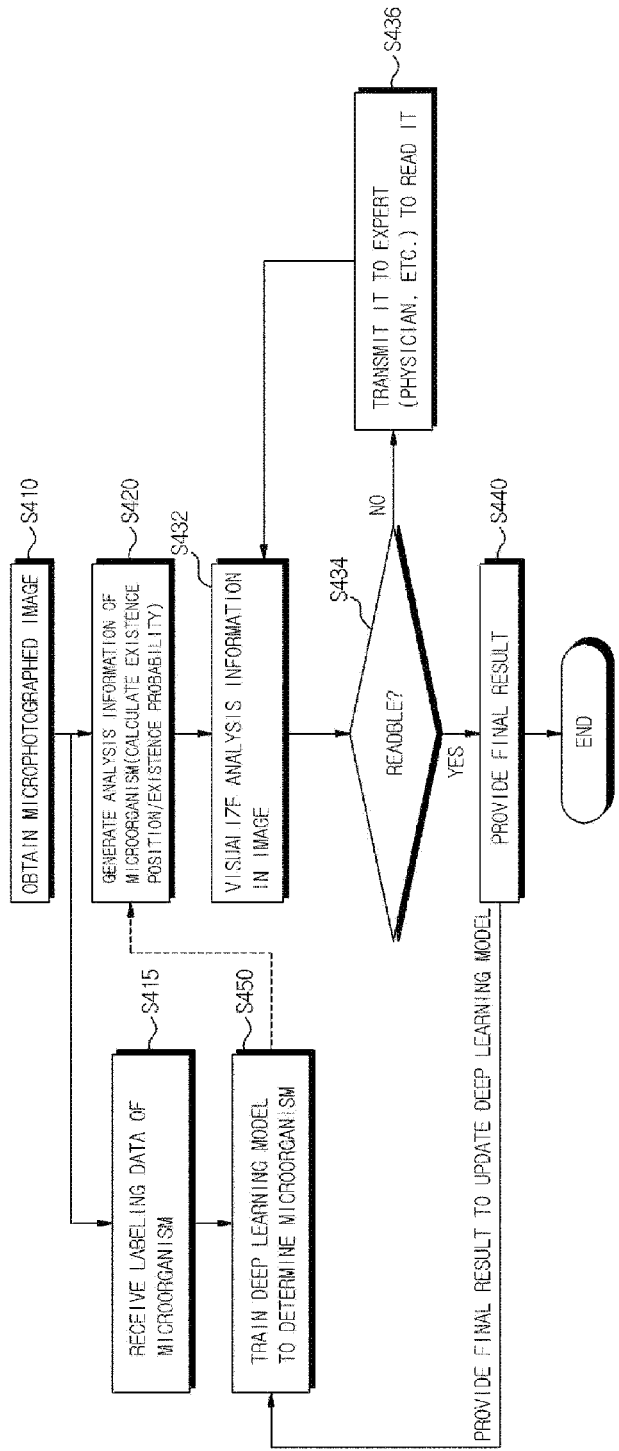
[Fig. 4]

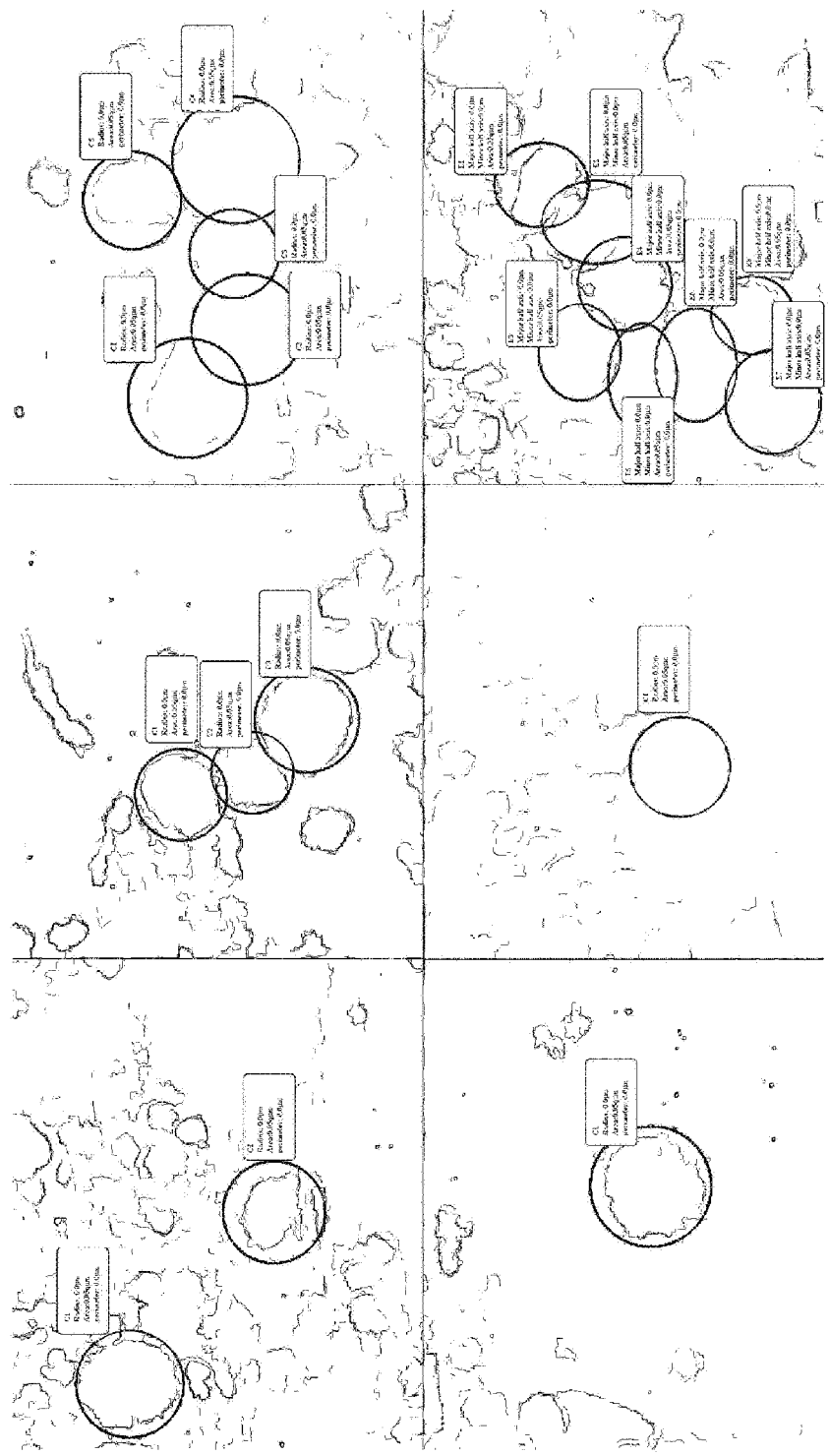
[Fig. 5]

METHOD FOR DETERMINING WHETHER EXAMINEE IS INFECTED BY MICROOGANISM AND APPARATUS USING THE SAME

CROSS REFERENCE TO RELATED APPLICATIONS

This application is a U.S. National Phase Application of International Application No. PCT/KR2018/000212 filed on Jan. 4, 2018, which claims the benefit of priority from Korean Patent Application 10-2017-0067838 filed on May 31, 2017, the disclosures of International Application No. PCT/KR2018/000212 and Korean Application No. 10-2017-0067838 are incorporated herein by reference.

TECHNICAL FIELD

The present invention relates to a method for determining whether an examinee is infected by microorganism, and an apparatus using the same. Specifically, the determination apparatus according to the present invention obtains an microphotographed image for a biological sample of the examinee, receives the obtained microphotographed image and generates analysis information on the microorganism based on a deep learning model for the microorganism infection disease, and visually provides the generated analysis information, so as to perform at least one of (i) a process to support a remote reading on whether there is microorganism corresponding to the analysis information, and (ii) a process to support a user to read whether there is microorganism corresponding to the analysis information, resultantly providing the final result. Further, the determination apparatus according to the present invention may make an update for the deep learning based on the final result.

BACKGROUND ART

In the modem society, sexually transmitted diseases may be easily treated. For example, while the infectious disease by *Trichomonas* may normally be treated with just 2 grams of drugs, the situation is that many people living in the developing countries do not get treatment yet since they do not even know their infections. According to WHO report, it is estimated that the prevalence rate of infectious diseases by *Trichomonas* in the world including Mongol is 30% or more, and it is known that the treatable sexually transmitted diseases that are targeted in "Global Health Sector Strategy on Sexually Transmitted Infections 2016-2021" may be treated with antibiotic only and its full recovery rate is 90% or more.

In case of developed countries, currently, the *Trichomonas* infection is determined through the means of PCR (Polymerase Chain Reaction) or the like, while a microscope is still utilized as a main inspection means in the third world countries such as Mongol, Philippine, etc. When utilizing this conventional inspection means, a medical staff identifies whether there is *Trichomonas*, through a small lens of a microscope. However, such method has a drawback that it is so repetitive that it not only takes long time for experienced physicians but also its accuracy becomes deteriorated. Especially, in case of the nonurban areas in the third world countries where medical infrastructure lags behind, a high-quality inspection is not sufficiently provided due to the problems such as skills of the microscopic inspection staffs.

Accordingly, the present invention suggests a method for determining whether an examinee is infected by microorganism, and an apparatus using the same, capable of solving such problems and supporting medical staffs to perform microscopic inspections more rapidly and precisely.

DISCLOSURE OF INVENTION

Technical Problem

It is, therefore, an objective of the present invention to enable a microorganism reading rapidly and precisely even while using an existing microscope by solving the above-mentioned problems.

Solution to Problem

The characteristic configurations of the present invention for achieving the objects of the present invention as described above and realizing the following characteristic effects of the present invention are as follows.

According to one aspect of the invention, there is provided a method for determining whether an examinee is infected by microorganism, including: (a) obtaining an microphotographed image of a biological sample of the examinee by a computing apparatus or supporting another apparatus that operates in conjunction with the computing apparatus to obtain the image; (b) receiving the obtained microphotographed image and generating analysis information on the microorganism based on a deep learning model of the microorganism infection disease by the computing apparatus, or supporting the another apparatus to generate the analysis information; (c) visualizing the generated analysis information to provide it by the computing apparatus, or supporting the another apparatus to provide the analysis information, so as to perform at least one of (i) a process of supporting a remote reading on whether the microorganism corresponding to the analysis information exists or not, and (ii) a process of supporting a user of the computing apparatus to read whether the microorganism corresponding to the analysis information exists or not; and (d) providing a final result as a result of performing the step (c) by the computing apparatus.

Preferably, the method further includes (e) making an update for the deep learning model based on the final result by the computing apparatus.

According to another aspect of the invention, there is provided a computer program including instructions that are implemented to cause a computing apparatus to perform the above-mentioned method.

According to a further aspect of the invention, there is provided an apparatus for determining whether an examinee is infected by microorganism, including: a communication unit configured to obtain an microphotographed image of a biological sample of the examinee; and a processor configured to receive the obtained microphotographed image and generate analysis information on the microorganism based on a deep learning model of the microorganism infection disease, or support another apparatus that operates in conjunction with the communication unit to generate the analysis information, wherein the processor is configured to: visualize the generated analysis information to provide it through a predetermined display unit, or support the another apparatus to provide the analysis information, so as to perform at least one of (i) a process of supporting a remote reading on whether the microorganism corresponding to the analysis information exists or not, and (ii) a process to support a user of the computing apparatus to read whether the microorganism corresponding to the analysis information exists or not; and provide a final result as a result of performing the processes (i) and (ii).

Preferably, the processor of the apparatus is configured to make an update for the deep learning model based on the final result by the computing apparatus.

Advantageous Effects of Invention

According to the present invention, there is an effect that whether microorganism exists or not can be read more quickly and accurately than a conventional method in which a medical staff checks whether the microorganism exists or not with naked eyes through a microscope.

Further, according to the present invention, it is possible to utilize an advanced reading technique such as a deep learning technique without replacing a conventional microscope by using a shooting module utilizing the microscope.

In addition, according to the present invention, it is possible to innovate a workflow in a medical field by enabling remote reading.

The present invention has the effect that the determination performance can be continuously improved by using the method of the present invention.

BRIEF DESCRIPTION OF DRAWINGS

The above object and features of the present invention will become apparent from the following description of the preferred embodiments given in conjunction with the accompanying drawings.

FIG. 1 is a view illustrating a main concept to explain a deep learning model used in the present invention.

FIG. 2 is a conceptual view schematically illustrating an exemplary configuration of a computing apparatus for performing a method to determine whether an examinee is infected by microorganism according to the present invention.

FIG. 3 is a conceptual view illustrating a hardware and software architecture of a computing apparatus for performing a method to determine whether an examinee is infected by microorganism according to the present invention.

FIG. 4 is a flowchart illustrating a method for determining whether an examinee is infected by microorganism according to the present invention.

FIG. 5 is a view illustrating visualized analysis information in the method for determining whether an examinee is infected by microorganism according to the present invention.

BEST MODE FOR CARRYING OUT THE INVENTION

In the following detailed description of the present invention, reference is made to the accompanying drawings that show, by way of illustration, specific embodiments in which the invention may be practiced to clarify the objects, technical solutions and advantages of the invention. These embodiments are described in sufficient detail to enable those skilled in the art to practice the invention.

It should be understood that throughout the detailed description and claims of the present invention, the term 'microorganism' and its variations are not restricted to a protozoa called *Trichomonas* which is an exemplary one for a subject to which the present invention is applied, but they include various kinds of protozoa, parasite, and other bacteria and all kinds of disease causes that may be identified by the microscope.

Further, it should be understood that throughout the detailed description and claims of the present invention, the term 'biological sample' is various kinds of materials that may be taken from an examinee including blood, serum, urine, lymph, cerebrospinal, saliva, semen, vaginal secretions, etc. of the examinee.

Further, it is to be understood by those skilled in the art that throughout the detailed description and claims of the present invention, the term 'learning' refers to performing machine learning according to the procedure, particularly to performing deep learning in the present invention, and is not intended to refer to mental action such as human educational activities.

Further, it should be understood that throughout the description and claims of the present invention, the word 'comprise' and its variations are not intended to exclude other technical features, additions, components or steps. Other objects, advantages and features of the present invention will become apparent to those skilled in the art from the present specification, and in part from the practice of the present invention. The following examples and drawings are provided by way of illustration and are not intended to limit the present invention.

Moreover, the present invention encompasses all possible combinations of embodiments shown herein. It should be understood that various embodiments of the present invention are different, but need not be mutually exclusive. For example, certain features, structures, and characteristics described herein may be embodied in other embodiments without departing from the spirit and scope of the present invention in connection with one embodiment. It is also to be understood that the position or arrangement of the individual components within each disclosed embodiment may be varied without departing from the spirit and scope of the present invention. The following detailed description is, therefore, not to be taken in a limiting sense, and the scope of the present invention is to be limited only by the appended claims, along with the full scope of equivalents to those for which those claims are entitled, where properly explained. In the drawings, like reference numerals refer to like or similar functions throughout the several views.

Unless otherwise indicated herein or clearly contradicted by context, an item referred to as singular is intended to encompass a plurality of items unless the context otherwise requires. Further, in the following description of the present invention, detailed description of known related components or functions will be omitted when it may make the subject matters of the present invention unclear.

Hereinafter, preferred embodiments of the present invention will be described in detail with reference to the accompanying drawings, in order to enable those skilled in the art to easily practice the invention.

FIG. 1 is a view illustrating a main concept to explain a deep learning model which is used in the present invention.

Referring to FIG. 1, the deep learning model may be briefly explained as a multi-layered artificial neural network. That is, it is expressed as a deep neural network in the sense that the network has a deep structure. Further, as illustrated in FIG. 1, in a multi-layered network structure, each image feature is automatically extracted by training the network using a large volume of data with errors of objective function being to be minimized, so that the training of the network is being progressed. It is also expressed as interconnection of neurons in the human brain in a certain sense. Accordingly, it is considered as a prevailing artificial intelligence.

The deep learning model, especially, a CNN (Convolutional Neural Network) utilized according to the present invention is a model suitable to classify a two-dimensional image. This has an advantage in that it can be possible to extract various levels of features from low level features such as points, lines and planes to complex and meaningful high level features by connecting repeatedly a convolution layer producing feature maps from each area of the image using a plurality of filters and a sub-sampling layer which reduces the size of the feature map and extracts features that are unchangeable by the change of position and rotation, and to construct a classification model of a higher precision using the finally extracted feature as an input value of the existing classification model.

Next, FIG. 2 is a conceptual view schematically illustrating an exemplary configuration of a computing apparatus for performing a method to determine whether an examinee is infected by microorganism (hereinafter, referred to as "infection determination method") according to the present invention.

Referring to FIG. 2, a computing apparatus 200 according to an embodiment of the present invention includes a communication unit 210 and a processor 220, which may communicate with an external computing apparatus (not shown) directly and indirectly via the communication unit 210.

Specifically, the computing apparatus 200 may accomplish a desired system performance by using a combination of a typical computer hardware (for example, a device including a computer processor, a memory, a storage, an input device and an output device, and other components of an existing computing apparatus; a telecommunication device such as a router and a switch; and an electronic information storage system such as a network attached storage (NAS), a storage area network (SAN), and a computer software (that is, instructions that enable the computing apparatus to be functioned in a specific manner).

The communication unit 110 of such computing apparatus can transmit and receive requests and responses to and from other interworking computing apparatuses. As an example, such requests and responses may be made by the same TCP session. However, the present invention is not limited thereto and they may be transmitted and received as, for example, a UDP datagram. In addition, in a broad sense, the communication unit 110 may include a keyboard, a mouse, and other external input devices for receiving commands or instructions.

Further, the processor 220 of the computing apparatus may include hardware components such as an MPU (Micro Processing Unit) or CPU (Central Processing Unit), a cache memory, and a data bus. In addition, it may further include software components such as an operating system and applications performing specific objectives.

FIG. 3 is a conceptual view illustrating a hardware and software architecture of the computing apparatus for performing the method to determine whether an examinee is infected by microorganism according to the present invention.

Referring to FIG. 3, the computing apparatus 200 may include a shooting module 310 as a component of the computing apparatus 200, or may operate in conjunction with the shooting module 310. The shooting module may obtain an microphotographed image that is a microscopic image of 100 or more magnifications through a whole scan shot, for a biological sample of the examinee, for example, a sample of the vaginal secretion, through which a whole image of the sample may be generated as an image or a separated image.

Before obtaining the microphotographed image, the biological sample may be dyed in order to make it easy to determine according to the present invention. For example, such dying may be performed utilizing Gram stain or Giemsa stain, but however is not limited thereto, as understood by those skilled in the art.

Meanwhile, as a specific embodiment of the shooting module 310, meanwhile, the shooting module 310 may include a driving unit that carries a stage by a mechanical driving such that the shooting module continues to photograph the microscopic image and matches the individual images continuously photographed with one another, obtaining a whole scan image. That is, the driving unit to obtain the whole scan image may be mounted on the stage of the existing microscope and fixed thereto, which may provide an advantage that the existing microscope may be reused.

The individual images continuously photographed may be separated and stored, respectively, and one whole scan image may also be obtained by applying an image match algorithm once with respect to the stored individual images. In addition, a scheme may be possible to photograph continuously and simultaneously to match the images in real time so that the individual images continuously photographed are added to the whole scan image, and those skilled in the art may propose various methods to obtain the whole scan image from the individual images by a mechanical driving of the driving unit in the shooting module 310.

Next, the photographed whole scan image may be transferred to the learning module 320. In the learning module 320, labeling data marked by an expert (for example, a physician, especially, a medical imaging physician) which indicates whether microorganism such as *Trichomonas* exists in the whole scan photographed image and a certain area of the image is obtained and a deep learning model for the microorganism infection disease is trained using the labeling data. A huge volume of labeling data is needed to increase accuracy and reliability of the deep learning model, and the accuracy and reliability can be enhanced as the amount of the data becomes larger.

Referring back again to FIG. 3, the analysis module 330 receives the obtained microphotographed image and generates analysis information on the microorganism, based on the deep learning model trained as aforesaid. The analysis information will be described later.

Next, a visualization module 340 visualizes the analysis information including an existence probability and an existence position of the microorganism to provide a user with it.

A remote reading module 350 provides at least one external expert with the visualized analysis information, and supports the external expert to remotely read whether the microorganism exists or not, obtaining a result of the remote reading.

Then, the computing apparatus 200 may obtain a final result for whether the microorganism exists or not based on the information obtained from at least one of the user and the external expert, and a update module 360 may make an update for the existing deep learning model based on the final result.

A method for determining whether infected or not according to the present invention will now be described in detail with reference to FIG. 4. FIG. 4 is a flowchart illustrating a method for determining whether infected or not according to the present invention.

Referring to FIG. 4, the infection determination method according to the present invention, firstly, includes step (S410) in which the communication unit 210 of the computing apparatus 200 obtains an microphotographed image for a biological sample of the examinee or supports another apparatus that operates in conjunction with the computing apparatus to obtain the image.

In this step (S410), the microphotographed image may be obtained by the whole scan shot of the shooting module 310 that operates in conjunction with the computing apparatus 200, in which an example of the shooting module 310 has been described above.

Next, referring to FIG. 4, the infection determination method according to the present invention further includes step (S420) to enable the analysis module 330 embodied by the processor 220 of the computing apparatus 200 to receive the microphotographed image and generate analysis information on the microorganism or to support another apparatus to generate the information, based on the deep learning model for the microorganism infection disease.

The deep learning model for this is trained by the learning module 320 embodied by the processor 220 using a number of labeling information that is input in advance (S415), that is, information including (i) data of a number of microphotographed image, (ii) data indicating whether the microorganism exists in the number of microphotographed image, and (iii) data indicating which area of the corresponding image the individual microorganism exists in, if the microorganism exists. As described above, the deep learning model may be a CNN (Convolutional Neural Network).

In step (S420) described above, the analysis information may include an existence probability and an existence position of the microorganism. In order to generate such analysis information, step (S420) may specifically include step (S422, not shown) to enable the computing apparatus 200 to automatically search for a microorganism-like suspicious object that may be doubted as the microorganism based on the deep learning model; and step (S424, not shown) to enable the computing apparatus 200 to perform a process to produce a probability that the microorganism-like suspicious object is the microorganism as the existence probability of the microorganism and a process to produce a position of the microorganism-like suspicious object as the existence position of the microorganism.

Referring again to FIG. 4, next, the infection determination method according to the present invention further includes, by enabling the visualization module 340 embodied by the processor 220 of the computing apparatus 200 to visualize the generated analysis information and provide it or to support the another apparatus to provide it (S432), step (S430, not shown, S432 to S438) that performs at least one of (i) a process (S436) to support a remote reading on whether the microorganism corresponding to the analysis information exists or not, and (ii) a process (S438, not shown) to support a user of the computing apparatus 200) to read whether the microorganism corresponding to the analysis information exists or not.

In this step (S430), the visualization of the analysis information may be performed by labeling the microorganism corresponding to the analysis information in the microphotographed image and displaying the analysis information.

As an example, FIG. 5 is a view illustrating visualized analysis information through step (S430) in a method to determine whether an examinee is infected by microorganism according to the present invention. FIG. 5 illustrates 6 individual images, in which each of the individual images labels whether the microorganism exists or not and displays the existence probability indicating a certain degree of the microorganism existence.

For example, referring to FIG. 5, the analysis information is a portion of the visualization process which may be displayed in a digitized form or a diagrammatic form. Here, various shapes of labels that humans easily identify, such as diagrams, lines and arrows, may be displayed in the area doubted as the microorganism in the microphotographed image or the area identified to have the microorganism existence probability that is higher than a predetermined specific probability. For each existence probability, it may be possible to have the user identify the existence probability easily through color, line thickness, special indication, etc.

Particularly, displaying information about a possibility that the microorganism exists in the microphotographed image in a separate area by putting the separate area in the microphotographed image, and providing the information about the possibility in a readily identifiable form of numbers, letters, diagrams, colors or the like may help the user determine whether to review in depth if the microorganism exists in the corresponding area.

As an embodiment of step (S430) illustrated in FIG. 4, if it is determined that the user of the computing apparatus 200 may read whether the microorganism exists or not in the examinee using the analysis information visualized and provided in this way (S434), whether the microorganism exists or not may be input as the final result. However, if it is determined that whether the microorganism exists or not is not read by the user (S434), the remote reading module 350 embodied by the processor 220 of the computing apparatus 200 provides at least one expert with the visualized analysis information through the communication unit 210 so that the at least one expert may remotely read the analysis information and may obtain the result through the communication unit 210 (S436), obtaining the final result indicating whether the microorganism exists or not.

As another embodiment of step (S430), the computing apparatus 200 receives the reading results indicating whether the microorganism exists or not from both the user and the at least one expert. In the case where the reading results coincide with each other, the final result is obtained accordingly, and in the case where the reading results are different from each other, the final result may be obtained in the majority decision method in which a predetermined weight is applied for individual subjects. In this manner, those skilled in the art may propose various embodiments for step (S430).

In addition, the infection determination method according to the present invention further includes step (S440) of providing the user or the like with the obtained final result through the display or the like. Here, the final result refers to whether the microorganism exists or not in the examinee, the existence position, whether the examinee is infected or not by the microorganism, etc.

As described above, the infection determination method according to the present invention may determine whether infected or not by the microorganism based on the deep learning model that has been trained in advance. Accordingly, when the final result indicating whether infected or not is utilized as updating materials for the deep learning model, again, there is an advantage that the deep learning model may enable to train additionally so as to perform the reading more precisely. Therefore, an embodiment of the infection determination method according to the present invention to gain such advantage may further include step to enable the update module 360 embodied by the processor 220 of the computing apparatus 200 to make an update for the deep leaning model based on the final result.

In this manner, the present invention has, through all the embodiments described above, an effect that a fast and precise reading may be provided compared with the conventional microorganism existence identification method in which a medical staff reads whether the microorganism exists or not with naked eyes through the microscope.

The advantage of the technology described herein as the embodiments is that the burdens of the medical staffs can be largely reduced, who have to make precise determinations under the busy medical environments due to much diagnostic inspections daily. Using the deep learning technology, it may be possible to analyze and learn features and forms of infectious microorganism with the computing apparatus using a huge amount of training data, that is, the labeling data described above, where the infectious microorganism is difficult to discern by the naked eyes or even physicians may discern the features and forms only by trains of several years. According, it may aid the determination of even the case that the human physician may overlook or the case that it is difficult to determine whether infected or not. In summary, according to the technique of the present invention, there is an advantage that the quality and speed of determination is enhanced since screening information only, that is, the microorganism-like suspicious positions only are automatically suggested and it is sufficient for the medical staffs to check on the positions.

Meanwhile, there is a case where since it is difficult to make a precise decision in the local distant areas, sample should be transmitted to the upper authorities. Currently, there is a problem that the sample is transferred by person. However, using the remote reading according to the present invention, there may be an advantage that the medical cooperation system which is nearly the same as the proximity treatment can be possible.

It can be clearly understood by those skilled in the art that, based on the description of the above embodiments, the present invention may be accomplished by a combination of software and hardware, or by hardware alone. The objects of the technical solutions of the present invention or portions contributed to the prior art may be embodied in the form of program instructions that can be executed through various computer components and recorded on a computer-readable recording medium. The computer-readable recording medium may include program instructions, data files, data structures, and the like, alone or in combination. The program instructions recorded on the computer-readable recording medium may be those specially designed and constructed for the present invention or may be those known to those skilled in the art of computer software. Examples of the computer-readable recording medium include a magnetic medium such as a hard disk, a floppy disk and a magnetic tape, an optical recording medium such as a CD-ROM and a DVD, a magneto-optical medium such as a floptical disk, and a hardware device specially configured to store and execute program instructions such as a ROM, a RAM and a flash memory. Examples of the program instructions include a machine language code such as that generated by a compiler, as well as a high-level language code that can be executed by a computer using an interpreter or the like.

The hardware device described above may be configured to operate as one or more software modules for performing the process according to the present invention, and vice versa. The hardware device may include a processor, such as a CPU or a GPU, connected to a memory such as ROM/RAM for storing program instructions and configured to execute the instructions stored in the memory, and a communication unit that can exchange signals with an external device. In addition, the hardware device may include a keyboard, a mouse, and other external input devices for receiving instructions prepared by developers.

Although the present invention has been particularly shown and described above with reference to the embodiments and drawings that are limited to the specific materials such as the specific components, it is to be understood that the embodiments are merely provided to help understand a comprehensive understanding of the invention and the invention is not limited to the disclosed embodiments, but those skilled in the art will appreciate that various modifications and changes are possible from the above description.

Therefore, it will be recognized that the spirit of the present invention should not be construed as being limited to the above-described embodiments, and the accompanying claims and all of modifications and equivalents are within the scope of the invention.

The modifications and equivalents would include, for example, logically equivalent methods that would yield the same results as those of the method according to the present invention.

While certain embodiments have been described, these embodiments have been presented by way of example only, and are not intended to limit the scope of the disclosures. Indeed, the embodiments described herein may be embodied in a variety of other forms. Furthermore, various omissions, substitutions and changes in the form of the embodiments described herein may be made without departing from the spirit of the disclosures. The accompanying claims and their equivalents are intended to cover such forms or modifications as would fall within the scope and spirit of the disclosures.

What is claimed is:

1. A method for determining whether an examinee is infected by a microorganism, comprising:
   obtaining a microphotograph image of a biological sample of the examinee by a computing apparatus;
   receiving the obtained microphotograph image and generating analysis information on the microorganism based on a deep learning model of the microorganism infection disease by the computing apparatus,
   wherein the analysis information includes information on a region in which a microorganism-like suspicious object is detected based on probability information calculated by the deep learning model;
   visualizing, by the computing apparatus, the analysis information by labeling the region and marking the region based on the probability information;
   providing the visualized analysis information to a plurality of apparatuses by the computing apparatus in order to obtain reading results from the plurality of apparatuses as to whether or not the microorganism-like suspicious object related to the region is the microorganism; and
   providing a final result to a user apparatus determined by the computing apparatus based on the reading results,
   wherein when the reading results obtained from the plurality of apparatuses are inconsistent, the computing apparatus determines one of the reading results as the final result based on a weight preconfigured for each of the plurality of apparatuses.

2. The method of claim 1, further comprising:
   making an update for the deep learning model based on the final result by the computing apparatus.

3. The method of claim 1, wherein the microphotograph image is obtained by a whole scan shot of a shooting module that operates in conjunction with the computing apparatus.

4. The method of claim 1, wherein the analysis information further includes an existence position of the microorganism.

5. The method of claim 4, wherein
the probability information includes a probability that the microorganism-like suspicious object is the microorganism, as an existence probability of the microorganism, and
a process of generating a position of the microorganism-like suspicious object as the existence position of the microorganism, by the computing apparatus.

6. The method of claim 1, wherein the biological sample has been already dyed before obtaining the microphotograph image of the biological sample.

7. The method of claim 1, wherein the microorganism is *Trichomonas*.

8. The method of claim 1, wherein the biological sample is a vaginal fluid sample of the examinee.

9. A computer program product embodied on a computer readable medium instructions that are implemented to cause a computing apparatus to perform the method of claim 1.

10. An apparatus for determining whether an examinee is infected by a microorganism, comprising:
a communication unit configured to obtain a microphotograph image of a biological sample of the examinee; and
a processor configured to receive the obtained microphotograph image and generate analysis information on the microorganism based on a deep learning model of the microorganism infection disease,
wherein the analysis information includes information on a region in which a microorganism-like suspicious object is detected based on probability information calculated by the deep learning model,
wherein the processor is configured to:
visualize the generated analysis information by labeling the region and marking the region based on the probability information,
provide the visualized analysis information to a plurality of apparatuses in order to obtain reading results from the plurality of apparatuses as to whether or not the microorganism-like suspicious object related to the region is the microorganism; and
provide a final result, to a user apparatus, determined based on the reading results,
wherein when the reading results obtained from the plurality of apparatuses are inconsistent, the processor determines one of the reading results as the final result based on a weight preconfigured for each of the plurality of apparatuses.

11. The apparatus of claim 10, wherein the processor is configured to make an update for the deep learning model based on the final result.

12. The apparatus of claim 10, wherein the microphotograph image is obtained by a whole scan shot of a shooting module that operates in conjunction with the communication unit.

13. The apparatus of claim 10, wherein the analysis information further includes an existence position of the microorganism.

14. The apparatus of claim 13,
wherein
the probability information includes
a probability that the microorganism-like suspicious object is the microorganism as an existence probability of the microorganism, and
the processor is configured to generate a position of the microorganism-like suspicious object as the existence position of the microorganism.

* * * * *